United States Patent [19]
Sabee

[11] Patent Number: 5,219,633
[45] Date of Patent: Jun. 15, 1993

[54] COMPOSITE FABRICS COMPRISING CONTINUOUS FILAMENTS LOCKED IN PLACE BY INTERMINGLED MELT BLOWN FIBERS AND METHODS AND APPARATUS FOR MAKING

[75] Inventor: Reinhardt N. Sabee, Appleton, Wis.

[73] Assignee: Tuff Spun Fabrics, Inc., Appleton, Wis.

[21] Appl. No.: 932,325

[22] Filed: Aug. 19, 1992

Related U.S. Application Data

[63] Continuation of Ser. No. 672,529, Mar. 20, 1991.

[51] Int. Cl.$^5$ .................. B32B 5/26; B32B 7/10; B32B 31/08; B32B 31/20; B32B 31/30
[52] U.S. Cl. .................. 428/109; 156/62.4; 156/167; 156/176; 156/177; 156/178; 156/183; 156/206; 428/110; 428/112; 428/113; 428/114; 428/152; 428/163; 428/172; 428/286; 428/287; 428/294; 428/296; 428/302
[58] Field of Search .................. 156/62.4, 167, 176, 156/177, 178, 209; 428/152, 109, 110, 112, 113, 114

[56] References Cited

U.S. PATENT DOCUMENTS

| | | |
|---|---|---|
| 3,849,241 | 11/1974 | Butin et al. ............... 156/167 |
| 4,034,375 | 7/1977 | Wallin ....................... 428/294 |
| 4,041,203 | 8/1977 | Brock et al. ............... 428/157 |
| 4,153,664 | 5/1979 | Sabee ........................ 264/289 |
| 4,223,063 | 9/1980 | Sabee ........................ 428/224 |
| 4,353,946 | 10/1982 | Bowers ..................... 428/109 |
| 4,440,819 | 4/1984 | Rosser et al. ............. 428/294 |
| 4,647,492 | 3/1987 | Grant et al. .............. 428/294 |
| 4,830,915 | 5/1989 | Diaz-Kotti ................ 428/109 |
| 4,906,507 | 3/1990 | Grynaeus et al. ......... 428/294 |
| 4,910,064 | 3/1990 | Sabee ........................ 428/113 |
| 5,002,815 | 3/1991 | Yamanaka et al. ....... 428/109 |
| 5,077,116 | 12/1991 | Lefkowitz ................. 428/294 |

Primary Examiner—James C. Cannon
Attorney, Agent, or Firm—Ryan, Kees & Hohenfeldt

[57] ABSTRACT

A low cost, high web integrity fabric that can be economically produced and tailored to provide a variety of different combinations of characteristics and properties for different end uses. It is a fabric wherein the strength in any direction can be predetermined and also wherein the elasticity in any direction can be varied in a predetermined fashion. It is also a fabric that combines continuous filaments, ranging from elastomeric to non-elastic but elongatable to at least a minimum extent, for strength and elasticity with the predetermined indepth intermingling of fibrous melt blown webs for interlocking of the said continuous filaments in the formation of the integrated, fibrous and continuous filament matrix.

41 Claims, 4 Drawing Sheets

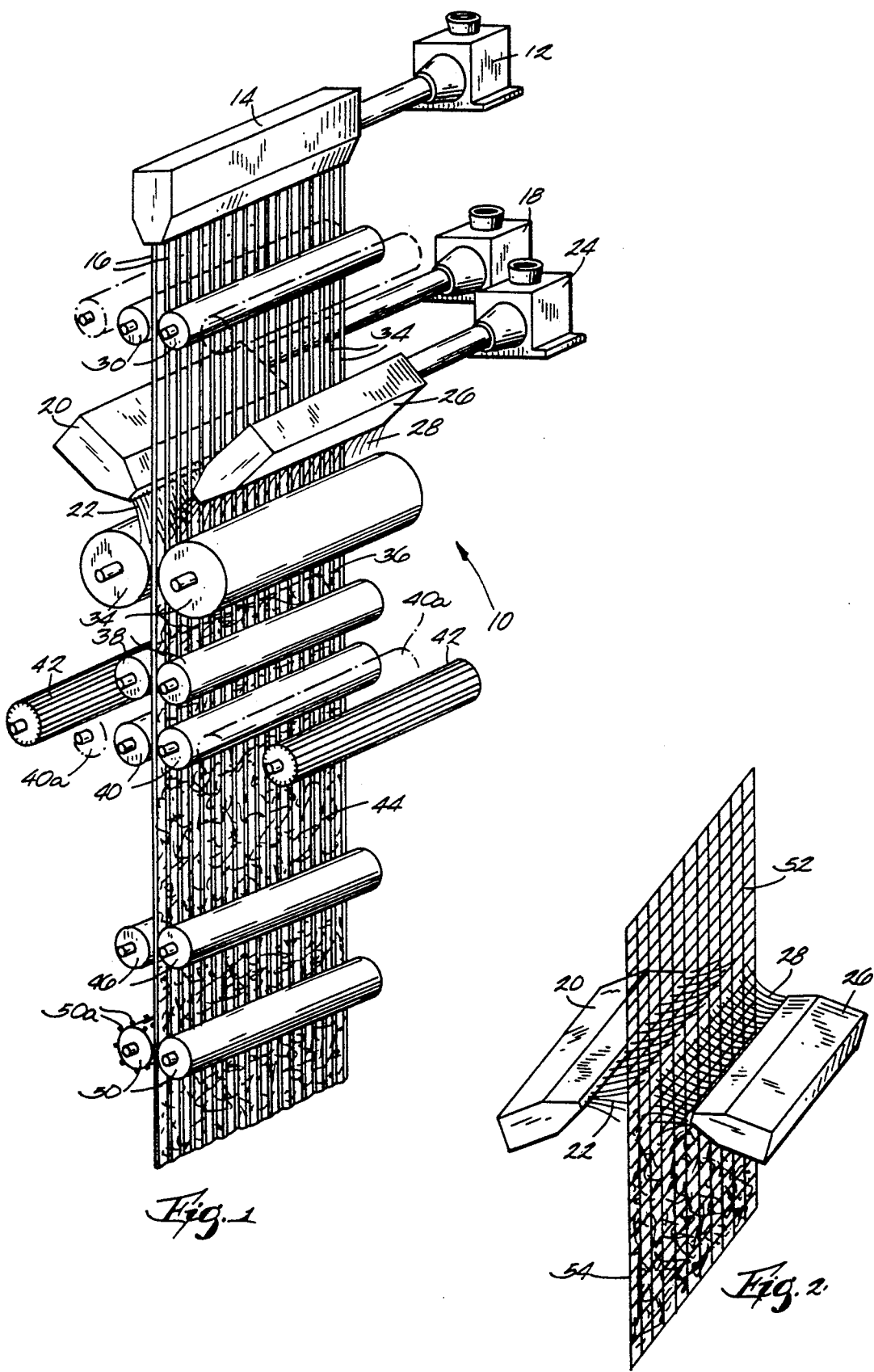

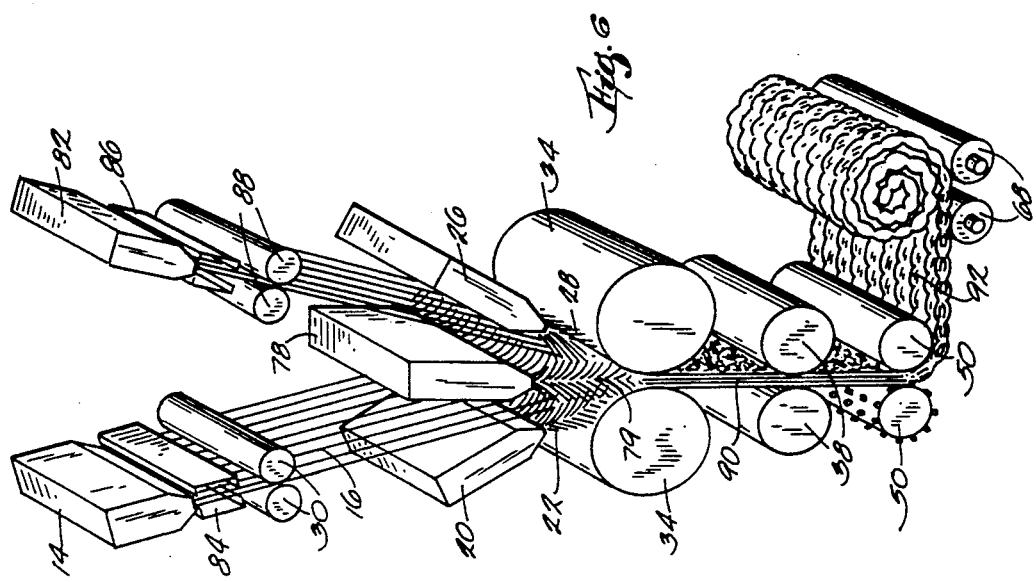
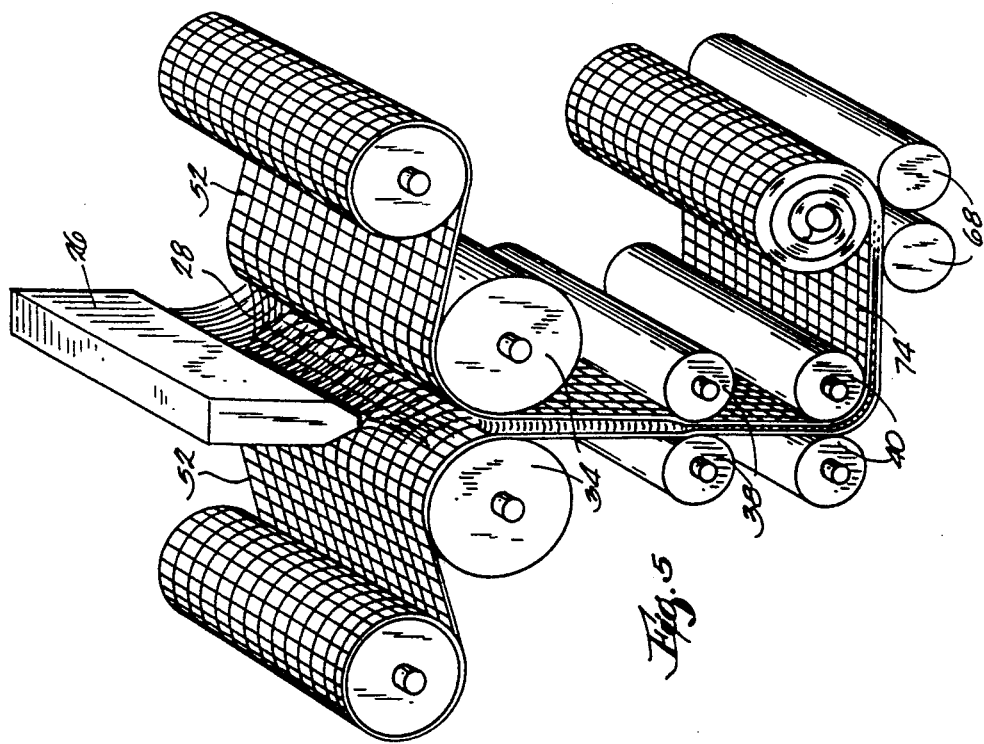

COMPOSITE FABRICS COMPRISING CONTINUOUS FILAMENTS LOCKED IN PLACE BY INTERMINGLED MELT BLOWN FIBERS AND METHODS AND APPARATUS FOR MAKING

CROSS-REFERENCE TO RELATED APPLICATION

This application is a continuation of application Ser. No. 07/672,529, filed Mar. 20, 1991.

BACKGROUND OF THE INVENTION

This invention pertains to low cost disposable composite fabrics, including elasticized fabrics, and a method and apparatus for making the same. More particularly, the present invention is concerned with at least one non-random laid continuous filament web joined with one or more melt blown webs, wherein the melt blown fibers of a first melt blown web intermingle with filaments of the non-random laid continuous filament web or intermingle with the fibers of a simultaneously deposited second web on the opposite side of the non-random laid web.

There has been a desire and great need in the disposable garment and diaper field for low cost disposable composite fabrics, including elasticized fabrics. The fabric should be:

1. elastic to provide a tight yet comfortable fit;
2. water repellent to retain fluids, yet be breathable to allow exchanges of vapors through the material;
3. have high bulk yet be soft, drapable with good hand and softness; and
4. opaque for use as disposable garments In addition there is a great need for a high strength fabric, low in cost and permitting fast stride-through of body fluids, which fabric can be formed by utilization of low cost machinery and an economical process.

The formation of the various prefabricated fibrous webs referred to herein is performed with the use of melt blowing techniques for forming fibers. These melt blowing techniques for forming fibers from thermoplastic resins, elastomeric fibers and non-elastic but elongatable fibers, can be prepared by known techniques as described in an article by Van A. Wente entitled "Superfine Thermoplastic Fibers" appearing in *Industrial and Engineering Chemistry*, Vol. 48, No. 8, pp. 1342 to 1346.

Another publication dealing with melt blowing is Naval Research Laboratory Report 111437 dated Apr. 15, 1954. According to this publication, the melt blowing process comprises heating a fiber forming resin to a molten state and extruding it through a plurality of fine orifices into a high velocity heated gas stream which attenuates the extrudate to from the melt blown fibers. This process is further described in U.S. Pat. No. 3,849,241 to Butin et al., the disclosure of which is incorporated herein in its entirety by reference and relied upon.

This invention relates to provisions for solutions some of these needs.

SUMMARY OF THE INVENTION

The known composite non-woven fibrous fabrics formed to date do not have stabilized, non-random, laid, continuous filaments intermingled with melt blown fibers in between and around the continuous filaments, to join the melt blown fibers and the continuous filaments thereby locking the continuous filaments in place and forming an integrated, fibrously joined, layered fabric, in which the said layers cannot be separated without their destruction.

This invention, then, relates to low cost, high web integrity fabrics that can be economically produced and tailored to provide a variety of different combinations of characteristics and properties for different end uses. It is a fabric wherein the strength in any direction can be predetermined and also wherein the elasticity in any direction can be varied in a predetermined fashion It is also a fabric that combines continuous filaments, ranging from elastomeric to non-elastic but elongatable to at least a minimum extent, for strength and elasticity with the predetermined indepth intermingling of fibrous melt blown webs for interlocking of the said continuous filaments in the formation of the integrated, fibrous and continuous filament matrix.

Other objects and advantages of the invention will become apparent hereinafter.

DESCRIPTION OF THE DRAWING

FIG. 1 is a perspective view of an apparatus constructed according to one embodiment of the invention, showing the forming section of a high speed, low cost elasticized fabric forming machine.

FIG. 2 is a perspective view of an embodiment of the invention slightly modified from that shown in FIG. 1, showing two opposed melt blown dies which are simultaneously depositing two opposed gas-fiber streams onto a stabilized, cross-laid, continuous filament web.

FIG. 5 is a perspective view of an alternative embodiment of the invention, showing a machine for forming high bulk fibrous fabric with scuff resistant surfaces.

FIG. 6 is a perspective view of another alternative embodiment of the invention, showing a machine for making highly entangled fibers and continuous filament high bulk fabrics.

DESCRIPTION OF THE PREFERRED EMBODIMENTS

Figure 4:
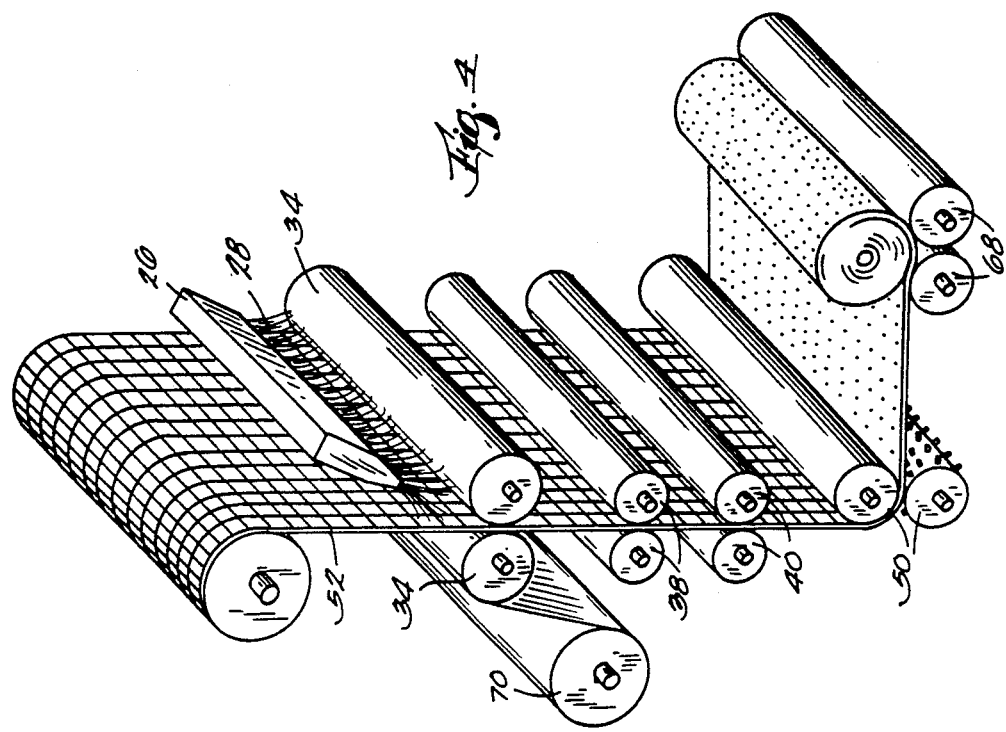
FIG. 4 is a perspective view of a further modification of the embodiment shown in FIG. 3, showing a machine for forming breathable absorbent fabrics.

In accordance with the present invention, then, low cost disposable fabrics, including elasticized fabrics of superior formation, strength and toughness are produced by the use of a stabilized continuous filamentary web, the manufacture of which is fully described in Sabee, U.S. Pat. No. 4,910,064, the disclosure of which is incorporated herein by reference and relied upon. It is this use of stabilized continuous filaments in combination with melt blown gas-fiber streams which, upon simultaneous deposition onto both sides of the stabilized continuous filaments, intermingle with each other and lock the continuous filaments in place by the joining of the two intermingled melt blown webs. These joinings or junctions range from mechanical entanglement to fusion bonding of the fibers This intermingled joining of the melt blown fibers whether it be mechanical intermingling only or fusion bonding ranging from stick bonds to full fusion bonds, is not a bond of the continuous filaments at their intersections. Hence the continuous filament intersections remain free to slip and slide over one another. This ability of the continuous filaments to slip and slide over one another during use drastically reduces the stiffness of the fabric and enhances the drape and hand. The improved drape and hand provided by this fabric, combined with the intermingling of the two opposing melt blown fibrous web surface fibers, form an integrated matrix of fibrous filaments and predetermined non-random laydown orientation of continuous filaments having a high cohesion and web integrity in a single step.

The intermingling of melt blown fibers with a predetermined laydown orientation of drawn, molecularly oriented continuous filaments coupled with the fusion bonding of the melt blown fibers insures the high degree of uniformity and strength in the formed fabric. This uniformity in fabric formation is especially advantageous in the formation of extremely light weight fabric, in which fiber and continuous filament forming materials may vary from elastomeric to non-elastic polymers and in which lower cost fiber forming materials must be used to meet competitive prices at the marketplace.

The terms "melt blown fibers", "melt blown fibers and/or filaments", and "melt blown fibers or filaments" are herein used interchangeably and refer to fiber lengths varying from short fibers to substantially continuous length filaments. Melt blown fibers may be adhesive fibers from materials including pressure sensitive, elastomeric, pressure sensitive elastomeric, hot melt or any fiberizable thermoplastic polymer, co-polymer or blend of polymers.

The continuous filaments are prepared by simultaneously spinning a multiple number of continuous filaments of a synthetic polymer such as a polypropylene or an elastomeric polymer through a multiple number of spinning nozzles or spinnerets, preferably extending in one or more rows. Upon exiting the spinnerets the filaments enter a controlled temperature chamber and are drawn away from the spinneret orifice at a greater rate than the rate of extrusion. Thus is effected a substantial draw down of the filaments in the molten state prior to solidification thereof. The solidified filaments having a low degree of molecular orientation are then subjected to a mechanical draw down with draw rolls under closely controlled temperature and velocity conditions thereby imparting a much higher degree of molecular orientation to the continuous filaments.

The melt blowing of adhesive fibers is performed by the same technique as in the previously discussed article by Van A. Wente, and have diameters ranging from less than 0.5 microns to more than about 250 microns. These adhesive fibers are made by extruding a molten thermoplastic adhesive material through a plurality of fine die capillaries as a molten extrudate of filaments into a high velocity gas stream which attenuates the filaments of molten adhesive material to reduce their diameter to the above stated range in the formation of microfibers or filaments. Any fiberizable hot melt adhesive material is suitable in the formation of adhesive fibers to be used in the intermingling and the joining of stratified fibrous fabrics. Elastomeric adhesives, pressure sensitive adhesives, pressure sensitive hot melts, visco-elastic hot melts, self-adhering elastic materials and conventional hot melt adhesives are some of the adhesives suitable for forming adhesive fibers. It is to be understood, however, that the present invention is not to be limited to these specific adhesives.

As has been previously stated, the melt blown adhesive fibers do not stiffen the fibrous stratified fabrics as do the roller applied or coated adhesives. These latter adhesives often fill crevices and interstices between the fibers of the fibrous layer or web and, after solidification, bind groups of fibers together, which stiffens the fibrous layer and has a deleterious effect on the hand and drape. The melt blown adhesive fibers on the other hand act as do the fibers of the layered fibrous web and not as sprays such as paint sprays, wherein small droplets of paint are emitted from the gun. The melt blown fibers, being flexible and of small diameter, are turbulently entangled with the fibrous web fibers and form bonds at their intersections with these fibers. These intersectional adhesive bonds behave similarly to fusion bonds with no noticeable stiffness of the composite fabric. They also provide the additional feature that the elastomeric adhesive fibers stretch or elongate under stress.

Other materials for use in forming indepth, joined, stratified webs are polyolefins such as polypropylene, polyethylene, polybutane, polymethyldentene, ethylene-propylene co-polymers; polyamides such as poly-hexamethylene adipamide, poly-(oc-caproamide), poly-hexamethylene sebacamide, polyvinyls such as polystyrene, thermoplastic elastomers such as polyurethanes, other thermoplastic polymers such as polytrifluorochloroethylene and mixtures thereof; as well as mixtures of these thermoplastic polymers and co-polymers; ethylene vinyl acetate polymers, synthetic polymers comprising 40% or more of polyurethane; polyetheresters; polyetherurethane; polyamide elastomeric materials; and polyester elastomeric materials S-EB-S Kraton "G" Block co-polymers and Kraton GX 1657 Block co-polymers as furnished by Shell Chemical Company; polyester elastomeric materials under the trade name "Hytrel" from the Dupont Company; polyurethane elastomeric materials under the trade name "Estane" from B. F. Goodrich and Company and polyamide elastomeric material under the trade name "Pebax" from Rilsam Company, including co-polymers, blends or various formulations thereof with other materials. Also included are visco-elastic hot melt pressure sensitive adhesives such as "Fullastic" supplied by H. B. Fuller and Company and other hot melt adhesives including pressure sensitive adhesives. Any of the fiber forming thermoplastic polymers including fiber forming hot melt adhesives, pressure sensitive adhesives, and visco-elastic hot melt pressure sensitive adhesives can be used for stabilizing the web or bonding the stabilized web to one or more cellulose webs, wood pulp webs, melt blown fibrous mats, or for laminating and bonding two or more stabilized webs to from laminates. The instant invention is not limited by the above polymers, for any thermoplastic polymer, co-polymer or mixture thereof capable of being melt blown into fibers or filaments is suitable. Any of the thermoplastic elastomers which are capable of being melt blown or melt spun are suitable for the manufacture of stretchable fabrics.

The continuous filaments used herein to form a curtain of continuous filaments can be of many materials, natural or manmade, ranging from textile threads or yarns composed of cotton, rayon, hemp, etc. to thermoplastic polymers. This invention is not limited to the use of any particular fiber, but can take advantage of many properties of different fibers. A curtain of continuous filaments or threads using multi-filament threads of rayon or nylon is readily stabilized by depositing a layer of molten melt blown fibers or filaments on this continuous filamentary web. Upon cooling, the molten melt blown filaments become tacky and self-bond to the continuous rayon or nylon threads.

In the preferred embodiments, thermoplastic melt spun continuous filaments are used which involve continuously extruding a thermoplastic polymer through a spinneret thereby forming a curtain of individual filaments. Among the many thermoplastic polymers suitable for the continuous filaments are polyolefins such as polyethylene and polypropylene; polyamides, polyesters such as polyethylene terepthalate; thermoplastic elastomers such as polyurethanes; thermoplastic copolymers; mixtures of thermoplastic polymers; co-polymers and mixtures of co-polymers; as well as the previously listed materials used herein for the melt blown fibers and filaments. However, the present invention is not limited to these materials, for any melt spinnable polymer is suitable, including all adhesive materials and spun bonded materials, for any melt spinnable polymer is suitable, including all adhesive materials and spun bonded materials listed herein, and melt blown materials. Other spinnable thermoplastic elastomers which are suitable for stretchable fabrics include but are not limited to polyester based polyurethane, and polyester type polyurethane polymeric fiber forming elastomers such as Texin 480A supplied by Mobay Chemical Company.

It will be understood that this invention is not to be limited to the aforementioned materials. On the contrary, it is intended that all fiberizable thermoplastic polymers, co-polymers and blends thereof, in addition to wood pulp or cellulose fibers and including staple fibers and equivalents as may be included within the spirit and scope of the invention as defined by the appended claims are to be included.

Referring now to FIG. 1, there is shown the forming section of a high speed, low cost, elasticized fabric forming apparatus 10 which is also capable of producing non-elastic, high strength, high bulk, opaque light weight fabrics for use in disposable garments. Apparatus 10 is also capable of forming combinations of both elastic and non-elastic properties in the same fabric for special uses.

Apparatus 10 includes three extruders: extruder 12 is provided with a melt spun die head 14 for forming molten elastomeric continuous filaments or molten non-elastic but elongatable filaments, both referenced by numeral 16; extruder 18 is provided with melt blown die head 20 for melt blowing fibers and/or filaments 22; and extruder 24 is provided with melt blown die head 26 also for melt blowing fibers and/or filaments 28.

If an elasticized web is to be formed, an elastomeric material of an elastomeric thermoplastic polymer such as Kraton G2730X which is also a styrenic block co-polymer comprising styrene end blocks with rubber mid-blocks, (SEBS Styrene-Butylene-Styrene), or Kraton D2120X which is also a styrenic block co-polymer comprising styrene end blocks with rubber midblocks, (SBS Styrene-Butadiene-Styrene), is fed into the hopper of extruder 12 and formed into one or more rows of molten continuous elastomeric filaments 16 by the die head 14 which contains one or more rows of spinnerets or capillary nozzles. The molten elastomeric filaments 16 are cooled, solidified and stretched as they are drawn from the nozzles by counter-rotating temperature controlled pull rolls 30. The cooled, solidified, stretched filaments 32 are subsequently pulled, while under tension, into the nip of a pair of temperature controlled deposition rolls 34 simultaneously with the deposition of two opposing melt blown gas-fiber streams or sprays 22 and 28 which are simultaneously and turbulently intermingled with each other and between the tensioned continuous elastomeric filaments 34. Thus is formed a fabric 36 comprising an integrated fibrous matrix of heat softened fibers and physically entrapped and mechanically entangled, tensioned, continuous elastomeric filaments.

This tensioned, coalesced fabric 36 may be further stretched or elongated, if desired, by stretching the fabric between the feed rolls 38 and the higher surface velocity of the draw rolls 40. Alternatively, the fabric 36 may be stretched or elongated by the use of the incremental stretch rolls 42, which then replace draw rolls 40. Draw rolls 40 may be withdrawn to the positions shown in phantom at 40a, for example. The incremental stretch rolls 42 then incrementally stretch the fabric 36 as further described in U.S. Pat. No. 4,223,063 and U.S. Pat. No. 4,153,664. The elongated fabric 44 containing stretched elastomeric filaments 16 is subsequently relaxed upon exiting from the pull rolls 46, and upon contracting, forms gathers in the melt blown depositions 22 and 28 of the relaxed fabric 48 which is subsequently wound into rolls.

If further bonding or additional compacting is desired, the elongated fabric 44 may be passed through a pair of temperature controlled embossing rolls 50, in place of or in addition to pull rolls 46. Generally, one of the rolls 50 is smooth while the other roll contains a plurality of raised projections 50a that form autogenous or fusion bonds at the raised point or projection locations. This process is further described in Sabee '064 and in Brock et al., U.S. Pat. No. 4,041,203, and is hereafter referred to as "pin-bonding".

Enhanced fusion bonding at the intersection of fibers 22 and 28 with each other and fusion bonding of fibers 22 and 28 with molten filaments 16, are obtained by disengaging pull rolls 30, that is, by repositioning them to the positions shown in phantom in FIG. 1. Also, the distance between the extrusion dies 20 and 26 and the molten continuous filaments 34 may be varied. In this manner, heat softened melt blown fibers 22 and 28 are able to intermingle with the heat softened continuous elastomeric filaments 16 while all the fibers 22 and 28 and the continuous filaments 16 are in the heat softened plastic state.

If a non-elasticized fabric is to be formed, it is only necessary to replace the elastomeric material in the extruder 12 with any thermoplastic polymer which will form continuous filaments upon being exited from the spinneret 14 orifices upon the application of heat and pressure. A thermoplastic melt spinnable polymer is fed into the hopper of extruder 12 and formed into one or more rows of molten continuous filaments 16 and processed as previously described in the processing of elastomeric fabrics. However, upon stretching between the feed rolls 38 and the draw rolls 40, followed by a relaxing step, the fabric does not contract as does the elasticized fabric, but remains substantially at its elongated length. The amount of recovery after stretching varies with the polymers used and their formulations. The resultant filaments are molecularly oriented in the longitudinal direction, resulting in a smaller diameter, longer and higher strength non-elastic filament as further described in Sabee '064.

FIG. 2 shows a stabilized non-random filamentary web 52 which is further described in Sabee '064, receiving two opposing simultaneous depositions of melt blown fibers 22 and 28 from two opposing die heads 20 and 26. These fibers 22 and 28 are turbulently intermingled with each other and the non-random laid continuous filaments of web 52, while forming fusion bonds which lock the continuous filaments in place. Only a small portion of the intermingled fibers need be intermingled with each other and between and around the continuous filaments to increase tremendously the tenacity of the fibrous joining, which results in the forming of the integrated fibrously joined layered fabric 54.

The simultaneous deposition of fibers, in a heat softened nascent condition, forms fusion bonds far superior to the fusion bonds formed by the deposition of fibers onto an already formed web wherein the fibers are already solidified. The surfaces of freshly formed fibers in a heat softened condition or in a soft nascent condition at elevated temperatures form highly coherent fusion bonds, since the surfaces are more compatible to surface fusion at lower temperatures, than does a heat softened fiber which is to be fusion bonded to a previously formed, cooled, and solidified fibrous web.

Figure 3:
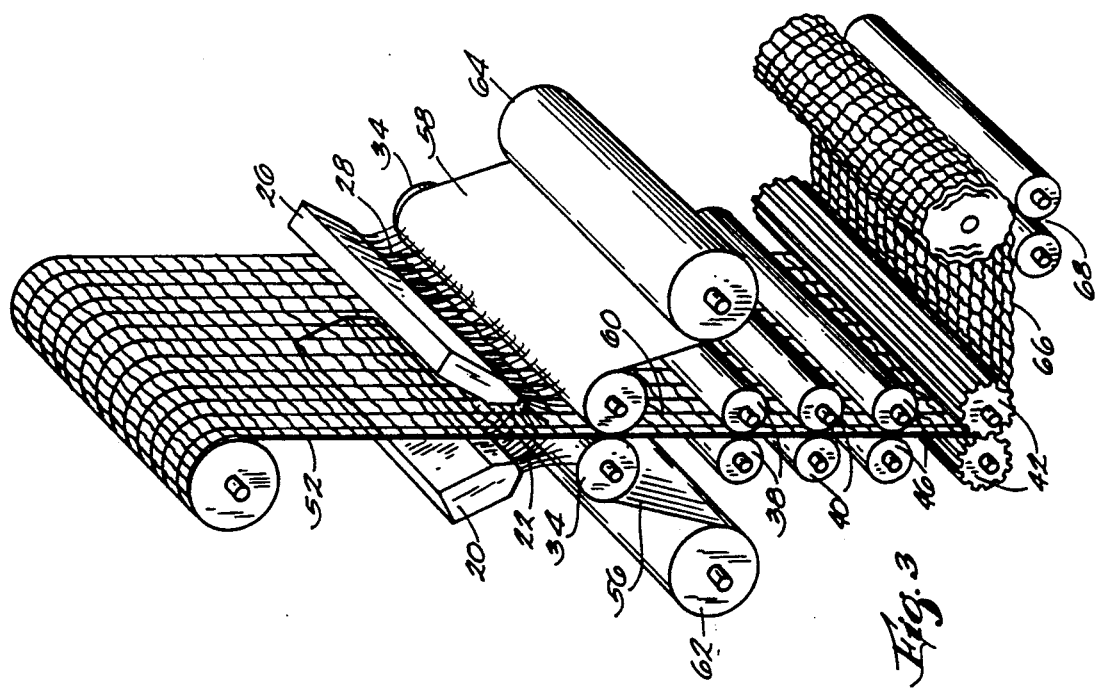
FIG. 3 is a perspective view of a further modification of the embodiment shown in FIG. 2, showing an elasticized fabric forming machine.

Webs comprising stabilized continuous elastomeric filaments intersecting each other as disclosed in Sabee '064, and as shown in FIG. 2 of this application, form the basic or precursor web for forming fabrics of high strength or elasticity in two or more directions. FIG. 3 shows a stretched, stabilized, elastic, non-random-laid filamentary web 52 receiving two opposing depositions of melt blown fibers 22 and 28 simultaneously as the stabilized web is passing through the nip of two temperature controlled deposition rolls 34. At the same time, deposition rolls 34 and/or additional prefabricated webs 56 and 58 are also receiving simultaneously melt blown depositions of fibers, thereby forming stretched elasticized fabric 60. This embodiment is useful in cases where it is required that the outer surfaces of fabric 60 have a high scuff or abrasion resistance. Webs 56 and/or 58 are fed from parent rolls 62 and 64 and bonded to web 52 in the nip of deposition rolls 34. Webs 56 and 58 may be any suitable prefabricated web including but not limited to dry or wet laid webs, spun bonded webs, melt blown webs, air laid webs, hydroentangled webs, film, spun laced webs, fibrillated films, needle punched webs, high loft fabrics, and stabilized, non-random laid, continuous filament webs as described in Sabee '064. The incremental stretch rolls 42 then incrementally stretch or corrugate the fabric 60, resulting in expanded or corrugated fabric 66, which may then be accumulated on a roll, for example by a two drum winder 68.

Another variation of fabric formation is shown in FIG. 4 wherein a prefabricated high loft web 70 is fed over one of the two deposition rolls 34, while melt blown fibers 28 from die head 26 are simultaneously and turbulently deposited into the nip of deposition rolls 34 in an intermingling fashion with the non-random laid continuous filament web 52, thereby forming the breathable absorbent fabric 72. Additionally, if desired, adhesive fibers from another die hard (not shown) may be simultaneously deposited and turbulently intermingled with web 52 and fibers 28 for increased bonding to web 70. Fabric 72 is then stretched if web 52 is elasticized, or lightly tensioned if web 52 is non-elastic, by adjusting the velocity differential between feed rolls 38 and the draw rolls 40. The web 72 may then be pin-bonded and accumulated as described above with respect to FIG. 3.

The composite fabric 74 of FIG. 5 is desired to have high scuff or abrasion resistant outer surfaces. To form this fabric 74, two stabilized non-random laid continuous filament webs 52 are fed over deposition rolls 34 with the simultaneous deposition of melt blown fibers 28 therebetween. These fibers 28 are, upon and during deposition, turbulently intermingled with themselves and the two webs 52 to form at least some fusion bonds with the non-random laid continuous filaments of the webs during the forming of high bulk web 76. Web 76 is then passed through feed rolls and draw rolls 40 for proper tensioning and bulk control to form high bulk scuff resistant fabric 74 and subsequently wound into rolls on the two drum winder 68.

Extremely high bulk fabrics suitable for air filtration are obtained by intermingling portions of two or more fiber streams of melt blown filaments when they are cooled sufficiently so as to have little or no fusion bonding and when the fibers are substantially turbulently intermingled before their deposition onto the collecting surface. Melt blown fibers when deposited in a heat softened condition bend and easily form and nest to the deposition surface, whether it be a smooth or a rough fibrous surface and upon cooling forms much denser webs than do fibers which have been cooled to solidification and thereafter turbulently intermingled with portions of two or more solidified fiber streams before their depositions onto a collecting surface. This is because the cooled, solidified fibers have taken various shapes upon solidification and have become rigid and fixed in these shapes, and upon deposition onto a collection surface do not nest together but form loose springy batts, which flatten under pressure and expand upon release of the pressure. These loose springy batts are not as dense as those made from a single die as taught in Butin et al. '241, but rather form high loft springy resilient fabrics, since the fibers were not formed into nested positions upon collection.

An example of a composite fabric of high bulk as formed according to this invention is shown in FIG. 6 and combines the melt blown streams 22, 28 and 79 of three spinneret die heads 20, 26 and 78 with the stabilized, cooled continuous filaments 16 and 80 being drawn from two melt spinning dies 14 and 82 through two cooling chambers 84 and 86 by pull roll sets 30 and 88. These streams 22, 28, 79 and filaments are combined, alternately and simultaneously, at the nip of temperature controlled deposition rolls 34. The melt blown filaments are solidified and intermingled with each other and with the continuous filaments, the outer fibrous layers being melt blown fibers 22 and 28. The newly formed composite high bulk fabric 90 may now be fed to a two drum winder 68 by feed rolls 38, or alternately pin-bonded at temperature controlled embossing rolls 50. In this embodiment the raised projections of the embossing roll 50 are preferably larger, longer and spaced further apart than those disclosed previously, to form the dimple embossed composite high bulk fabric 92.

Figure 7:
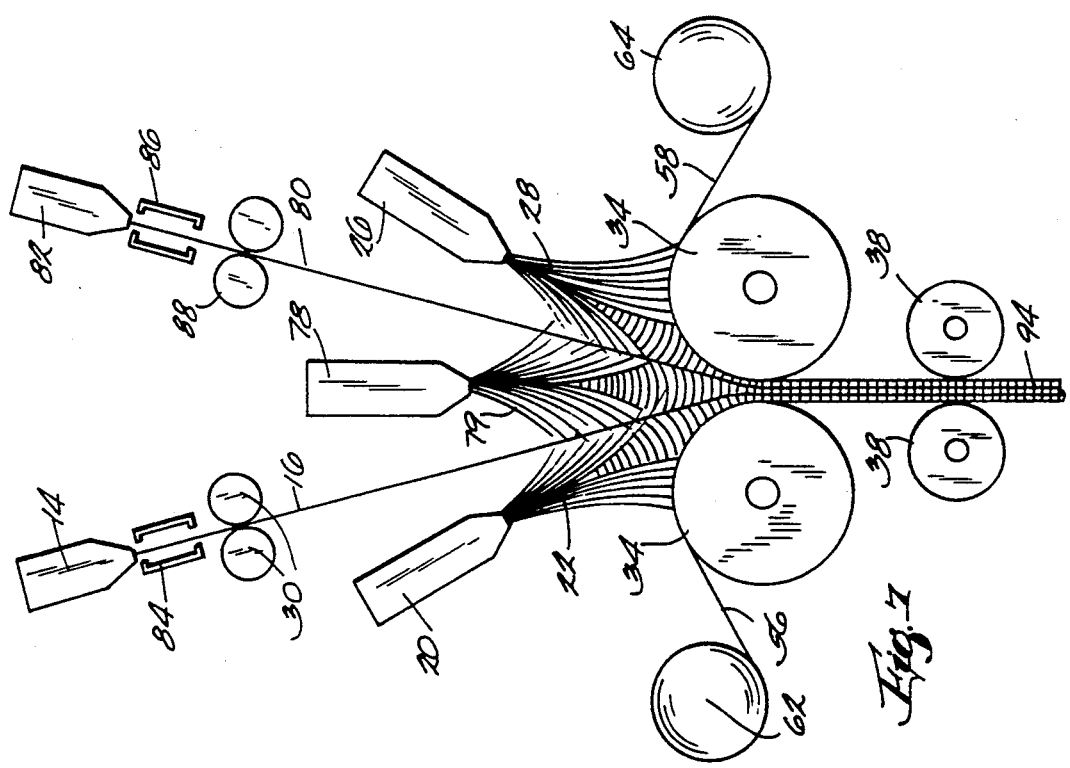
FIG. 7 is an end view of an apparatus which is a slight modification of that shown in FIG. 6, showing optional parent rolls.

FIG. 7 is an end view of a fabric forming machine similar to that shown in FIG. 6. FIG. 7 very clearly shows the simultaneous intermingling and deposition of melt blown fibers 22, 28 and 78 with the stabilized elastomeric continuous filaments 16 and 80 being drawn from two melt spinning dies 14 and 82, through two cooling chambers 84 and 86 by pull roll sets 30 and 88 and combined, alternately and simultaneously, at the nip of temperature controlled deposition rolls 34. The melt blown filaments 22, 79 and 28 are intermingled with each other and with the continuous filaments 16 and 80, the outer fibrous layers being melt blown fibers 22 and 28. This embodiment provides for parent rolls 62 and 64, carrying webs 56 and 58. Webs 56 and 58 may be fed into the nip of rolls 34 to form protective covers for a resulting elasticized composite high bulk fabric 94.

While the apparatus hereinbefore described is effectively adapted to fulfill the aforesaid objects, it is to be understood that the invention is not intended to be limited to the specific preferred embodiment of composite fabrics comprising continuous filaments locked in place by intermingled melt blown fibers, and methods for making, as set forth above. Rather, it is to be taken as including all reasonable equivalents within the scope of the following claims.

I claim:

1. A process for producing a composite non-woven fabric, said process comprising:
   a) providing at least one extruder with melt spinning die heads having a multiple number of melt spinning nozzles;
   b) extruding thermoplastic polymeric continuous elastomeric filaments from said nozzles;
   c) drawing said polymeric continuous elastomeric filaments from said nozzles with a pair of temperature controlled feed rolls;
   d) providing at least two extruders having a multiple number of melt blown nozzles;
   e) feeding said continuous elastomeric filaments into a nip of a pair of counter-rotating temperature controlled deposition rolls under no tension;
   f) depositing at least two opposing melt blown fiber streams, at least one of which is elongatable but not elastic, onto said continuous elastomeric filaments prior to feeding said continuous elastomeric filaments into said temperature controlled deposition rolls where they intermingle with each other and with said untensioned continuous elastomeric filaments;
   g) feeding said assembly into the nip of said pair of counter-rotating temperature controlled deposition rolls under no tension thereby forming said composite fabric;
   h) feeding the said solidified composite non-woven fabric between said deposition rolls and a pair of draw rolls, having a higher surface velocity, thereby stretching the said continuous elastomeric filaments and elongating the elongatable but non-elastic melt blown fibrous web;
   i) relaxing the elongated composite fabric thereby forming buckles and gathers in the fibrous non-woven gatherable web.

2. The process according to claim 1 wherein steps e, f and g are done simultaneously.

3. The process according to claim 1 wherein at least one additional melt blown fiber stream comprising thermoplastic polymeric adhesive fibers is deposited simultaneously with said intermingled melt blown fiber streams.

4. The process according to claim 1 wherein at least some of the melt blown fiber streams deposited into the nip of the said temperature controlled deposition rolls are elastomeric.

5. The process according to claim 1 wherein at least some of the continuous filaments are elongatable but non-elastic.

6. The process according to claim 1 wherein at least one suitable prefabricated web is fed into the nip of said temperature controlled deposition rolls.

7. The process according to claim 6 wherein the at least one suitable prefabricated web is selected from the group consisting of: dry or wet laid webs, spun bonded webs, melt blown webs, air laid webs, hydroentangled webs, film, spun laced webs, fibrillated films, needle punched webs, high loft fabrics, and stabilized, non-random laid, continuous filament webs, each of which comprises at least some super absorbent materials.

8. The process according to claim 1 wherein at least some of the continuous filaments lie in a predetermined transverse direction to each other, there being intersections between such transverse filaments.

9. The process according to claim 8 wherein at least some of the continuous filament intersections are free to slip and slide over one another.

10. A composite non-woven fabric produced by the process of claim 1.

11. A process for producing a composite non-woven fabric, said process comprising the steps of:
   a) providing at least two elastomeric filamentary curtains, each comprising a multitude of elastomeric continuous filaments laid down in a predetermined non-random orientation;
   b) depositing at least one deposition of melt blown non-elastic but elongatable fibers between said elastomeric filamentary curtains;
   c) feeding said melt blown fibrous deposition, faced on both surfaces with stabilized elastomeric filamentary curtains, into a nip between two temperature controlled deposition rolls thereby forming said composite non-woven fabric;
   d) stretching the solidified composite non-woven fabric between said deposition rolls and a pair of draw rolls having a higher surface velocity, thereby stretching the said elastomeric continuous filaments and elongating the said melt blown non-elastic but elongatable fibrous web;
   e) relaxing the elongated non-woven composite fabric thereby forming buckles and gathers in the fibrous non-woven gatherable web.

12. The process according to claim 11 wherein steps b and c are done simultaneously.

13. The process according to claim 11 wherein during step c the elastomeric continuous filaments are not subjected to tension.

14. The process according to claim 11 wherein during step c the elastomeric continuous filaments are under tension.

15. The process according to claim 11 wherein the surfaces of said composite fabric are scuff resistant.

16. The process according to claim 11 wherein said composite fabric is absorbent and breathable.

17. The process according to claim 11 wherein said composite fabric comprises at least some substantially continuous melt blown fibers or filaments.

18. The process according to claim 11 wherein said composite fabric is autogenously bonded by a pair of temperature controlled pin or dimple embossing rolls.

19. The process according to claim 11 wherein said melt blown fibers comprise polypropylene polymers.

20. The process according to claim 11 wherein said melt blown fibers comprise polyester polymers.

21. The process according to claim 11 wherein said melt blown fibers comprise a mixture of polypropylene and polyester polymers 22. The process according to claim 11 wherein at least some of the continuous filaments lie in a predetermined transverse direction to each other.

23. The process according to claim 11 wherein at least some of the melt blown filaments are elastomeric.

24. The process according to claim 11 wherein at least some of the melt blown filaments are elongatable but non-elastic.

25. The process according to claim 11 wherein at least some of the continuous filaments are non-elastic but elongatable.

26. The process according to claim 11 wherein at least one melt blown deposition is deposited directly onto at least one deposition roll.

27. The process according to claim 11 wherein at least one suitable prefabricated web is fed into the nip of said temperature controlled deposition rolls.

28. The process according to claim 27 wherein the at least one suitable prefabricated web is selected from the group consisting of: dry or wet laid webs, spun bonded webs, melt blown webs, air laid webs, hydroentangled webs, film, spun laced webs, fibrillated films, needle punched webs, high loft fabrics, and stabilized non-random laid, continuous filament webs, each of which comprises at least some super absorbent materials.

29. The process of claim 11 further comprising, prior to step c, the step of adding at least one additional deposition of melt blown fibers to said outer surfaces of said elastomeric filamentary curtains.

30. The process according to claim 29 further comprising, prior to step 3, the step of adding at least one prefabricated web.

31. The process of claim 11 wherein at least some of the continuous filaments are elongatable but non-elastic and comprise polyethylene terepthalate, and wherein at least some of said melt blown fibers are comprised of polyethylene terepthalate.

32. A composite non-woven fabric produced by the process of claim 11.

33. A process for producing a composite fabric, said process comprising:
providing an unstretched elastomeric web;
depositing at least two opposing depositions of melt blown fibers onto said unstretched elastomeric web while simultaneously feeding the same into a nip comprising two deposition rolls and at least one suitable prefabricated web, thereby forming an untensioned elasticized fabric;
stretching and elongating the untensioned elasticized fabric; and
relaxing the elongated tensioned elasticized fabric to form buckles and gathers in the fibrous non-woven gatherable web.

34. The process according to claim 33 wherein at least one of said opposing depositions comprises adhesive fibers.

35. The process according to claim 34 further comprising depositing at least one melt blown deposition directly onto at least one deposition roll.

36. The process according to claim 33 wherein said elastomeric web comprises a web of continuous elastomeric filaments and wherein at least some of the continuous filaments lie in a predetermined transverse direction to each other.

37. The process according to claim 33 wherein the at least one suitable prefabricated web is selected from the group consisting of: dry or wet laid webs, spun bonded webs, melt blown webs, air laid webs, hydroentangled webs, film, spun laced webs, fibrillated films, needle punched webs, high loft fabrics, and stabilized, non-random laid, continuous filament webs, each of which comprises at least some super absorbent materials.

38. The process according to claim 33 wherein the unstretched elastomeric web comprises at least some melt blown elastomeric fibers.

39. The process according to claims 33 further comprising, prior to the relaxing step, pin bonding the elongated, tensioned, elasticized fabric.

40. The process of claims 33 wherein the step of depositing the melt blown fibers includes the deposition of at least some melt blown adhesive fibers.

41. A composite fabric produced by the process of claim 33.

* * * * *